(12) United States Patent
Pratx et al.

(10) Patent No.: US 10,175,219 B2
(45) Date of Patent: Jan. 8, 2019

(54) METHOD TO SORT CELLS ON THE BASIS OF RADIONUCLIDE UPTAKE

(71) Applicant: The Board of Trustees of the Leland Stanford Junior University, Palo Alto, CA (US)

(72) Inventors: Guillem Pratx, Mountain View, CA (US); Silvan Tuerkcan, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 131 days.

(21) Appl. No.: 14/743,382

(22) Filed: Jun. 18, 2015

(65) Prior Publication Data

US 2016/0025701 A1    Jan. 28, 2016

Related U.S. Application Data

(60) Provisional application No. 62/029,760, filed on Jul. 28, 2014.

(51) Int. Cl.
    *G01N 33/483* (2006.01)
(52) U.S. Cl.
    CPC .................. *G01N 33/4833* (2013.01)
(58) Field of Classification Search
    None
    See application file for complete search history.

(56) References Cited

U.S. PATENT DOCUMENTS

| | | | |
|---|---|---|---|
| 3,857,033 A | 12/1974 | Cobb | |
| 2003/0055307 A1* | 3/2003 | Elmaleh | A61B 5/0071 600/1 |
| 2005/0079131 A1* | 4/2005 | Lanza | B82Y 5/00 424/1.11 |
| 2008/0166795 A1* | 7/2008 | Shuler | C12M 23/16 435/288.7 |
| 2009/0220430 A1* | 9/2009 | Rajopadhye | A61K 49/0032 424/9.6 |
| 2010/0015051 A1* | 1/2010 | Labhasetwar | A61K 9/5153 424/1.69 |
| 2010/0284932 A1* | 11/2010 | Goutayer | A61K 49/0032 424/9.6 |

(Continued)

OTHER PUBLICATIONS

Gomes et al. "Fluorescence probes used for detection of reactive oxygen species" J. Biochem. Biophys. Methods 65 (2005) 45-80. (Year: 2005).*

(Continued)

*Primary Examiner* — Blaine Lankford
*Assistant Examiner* — Lauren K Van Buren
(74) *Attorney, Agent, or Firm* — Lumen Patent Firm

(57) ABSTRACT

A method of sensing radionuclides in cells is provided that includes exposing a cell of interest to a radiolabeled molecule, encapsulating the cell of interest with a chemical sensor in an encapsulant to hold the cell of interest and the chemical sensor in proximity, where the radiolabeled molecule decays to emit an energetic particle, and detecting a fluorescence or optical absorption signal in the chemical sensor induced by the radio molecule decay, using an illumination source and a detector, where single-cell analysis with the radiolabeled molecule is performed.

9 Claims, 9 Drawing Sheets

(56) References Cited

U.S. PATENT DOCUMENTS

2012/0276002 A1* 11/2012 Yoo .................... A61K 49/0002
424/1.49
2014/0242600 A1* 8/2014 Xing .................. G01N 21/6458
435/6.18
2016/0217878 A1* 7/2016 Nino ........................ G21H 1/12

OTHER PUBLICATIONS

Pratx "Radioluminescence Microscopy: Measuring the Heterogeneous Uptake of Radiotracers in Single Living Cells" PLOS One, Oct. 2012, vol. 7, Issue 10. (Year: 2012).*
Sun et al. Synthesis and Radioluminescence of PEGylated Eu3+ doped Nanophosphors as Bioimaging Probes, Adv. Mater 2011, 23, H195-H199. (Year: 2011).*
Sun et al. "Multifunctional Nanophosphors for Enhanced Tumor Radiotherapy" Proceedings of the 2011 World Molecular Imaging, P326 Congress, Sep. 10, 2011 (Year: 2011).*

* cited by examiner

*in vivo & in vitro*

METHOD TO SORT CELLS ON THE BASIS OF RADIONUCLIDE UPTAKE

CROSS-REFERENCE TO RELATED APPLICATIONS

This application claims priority from U.S. Provisional Patent Application 62/029,760 filed Jul. 28, 2014, which is incorporated herein by reference.

STATEMENT OF GOVERNMENT SPONSORED SUPPORT

This invention was made with Government support under grant number CA186275 awarded by National Institutes of Health. The Government has certain rights in this invention.

FIELD OF THE INVENTION

The present invention relates generally to molecular analysis of single cells. More particularly, the invention relates to using photostimulable phosphors or reactive oxygen species sensors to sort single cells according to their uptake of a radionuclide molecule.

BACKGROUND OF THE INVENTION

Molecular analysis using flow cytometry has opened new possibilities for observing the unique phenotypes of single cells. Today, flow cytometry is on the front lines of cancer research and is routinely used to measure gene expression, therapeutic response, DNA content, cycling, drug resistance, and cell-surface markers of single cells. While the advent of this technology has revolutionized cancer research, many important biochemical processes involving small molecules, such as drugs and metabolites, remain invisible to fluorescence probing. Quantitative detection of small molecules with conventional methods (e.g. liquid scintillation counting, mass spectroscopy) is possible, but only in bulk samples for lack of sufficient sensitivity. However, bulk measurements can be misleading because the ensemble average may not accurately represent the individual cell characteristics.

What is needed is a high-throughput single-cell scintillation counting system and method that can sort cells on the basis of the uptake of a small radiolabeled molecule.

SUMMARY OF THE INVENTION

To address the needs in the art, a method of sensing radionuclides in cells is provided that includes exposing a cell of interest to a radiolabeled molecule, encapsulating the cell of interest with a chemical sensor in an encapsulant to hold the cell of interest and the chemical sensor in proximity, where the radiolabeled molecule decays to emit an energetic particle, and detecting a fluorescence or optical absorption signal in the chemical sensor induced by the radioactive decay, using an illumination source and a detector, where single-cell analysis with the radiolabeled molecule is performed.

According to one aspect of the current invention, the chemical sensor includes molecules that are activated by reactive oxygen species having molecules that include oxygen, superoxide anion, peroxide, hydrogen peroxide, or hydroxyl radical and hydroxyl ion.

In a further aspect of the invention, the chemical sensor has molecules that include a mixture of tertiary-butyl acrylate and maleimido-pyrene, a solution of Ferrous Benzoic acid Xylenol orange, a solution of ferrous sulfate, 2,7-Dichlorodihydrofluorescein (DCFH), 7-hydroxy-6-methoxy-coumarin (Scopoletin), 3.3. N-Acetyl-3,7-dihydroxyphenoxazine (Amplex Red), Homovanillic acid (4-hydroxy-3-methoxy-phenylacetic acid); Dihydrorhodamine 123 (DHR), 4-(9-Anthroyloxy)-2,2,6,6-tetramethyl-piperidine-1-oxyl, 1,3-Cyclohexanedione, Sodium terephthalate, Coumarin, coumarin-3-carboxylic acid, N-succinimidyl ester of coumarin-3-carboxylic acid, 2-[6-(4V-Hydroxy)phenoxy-3H-xanthen-3-on-9-yl]benzoic acid, 2-[6-(4V-amino)phenoxy-3H-xanthen-3-on-9-yl] benzoic acid, storage phosphors (e.g. BaFBr:Eu2+ and CsBr:Eu2+, silver halide particles, ratiometric sensors, radiosensitive polymer, or cleavable FRET pair.

In another aspect of the invention, the radiolabeled molecules include molecules labeled with alpha or beta-emitting nuclides. In one aspect, the beta-emitting nuclides include $^{3}H$, $^{11}C$, $^{14}C$, $^{18}F$, $^{32}P$, $^{33}P$, $^{68}Ga$, $^{89}Zr$, $^{64}Cu$, $^{131}I$ or $^{35}S$.

According to one aspect of the invention, the encapsulant can include a gelling agent in water, a gelling agent in oil, an oil droplet in water, and a water droplet in oil.

In yet another aspect of the invention, the detecting is done using a device that includes a flow cytometer, a microfluidic channel, plate reader, or a microscope.

According to a further aspect of the invention, the chemical sensor is held in proximity to the cell by irreversibly being taken up by the cell or fixed to the cell membrane rather than being encapsulated with the cell.

BRIEF DESCRIPTION OF THE DRAWINGS

(FIG. 2B) Quantitative analysis of cell uptake; (FIG. 2C) Time-resolved measurement of FDG efflux in cancer stem cells; (FIG. 2D) Efflux rates, according to embodiments of the current invention.

DETAILED DESCRIPTION

Flow cytometry is widely used as a method to measure the biological state of large populations of single cells. It can measure three physical parameters of the cell: (1) forward scatter, (2) side scatter, and (3) fluorescence. While very useful, these three parameters do not provide a complete picture of the state of the cell. Most small molecules are not fluorescent and therefore cannot be used in flow cytometry. Many molecules can be rendered fluorescent by a fluorophore label, but this approach is not well suited for small molecules, because the large fluorophore would alter the size of the small molecule too much. Small molecules are usually quantified using bulk assays (e.g. radionuclide detection, mass spectrometry), which do not resolve single cells. The invention allows virtually any small molecule, including non-fluorescent molecules, to be measured in single cells, with high throughput, and using the already existing base of flow cytometers or other suitable device, such as a microfluidic channel, or a microscope. Therefore, it is the ideal method for quantifying small molecules in single cells. Furthermore, it can sort cells on the basis of this measurement, enabling new ways of defining subpopulations of cells.

Figure 1:
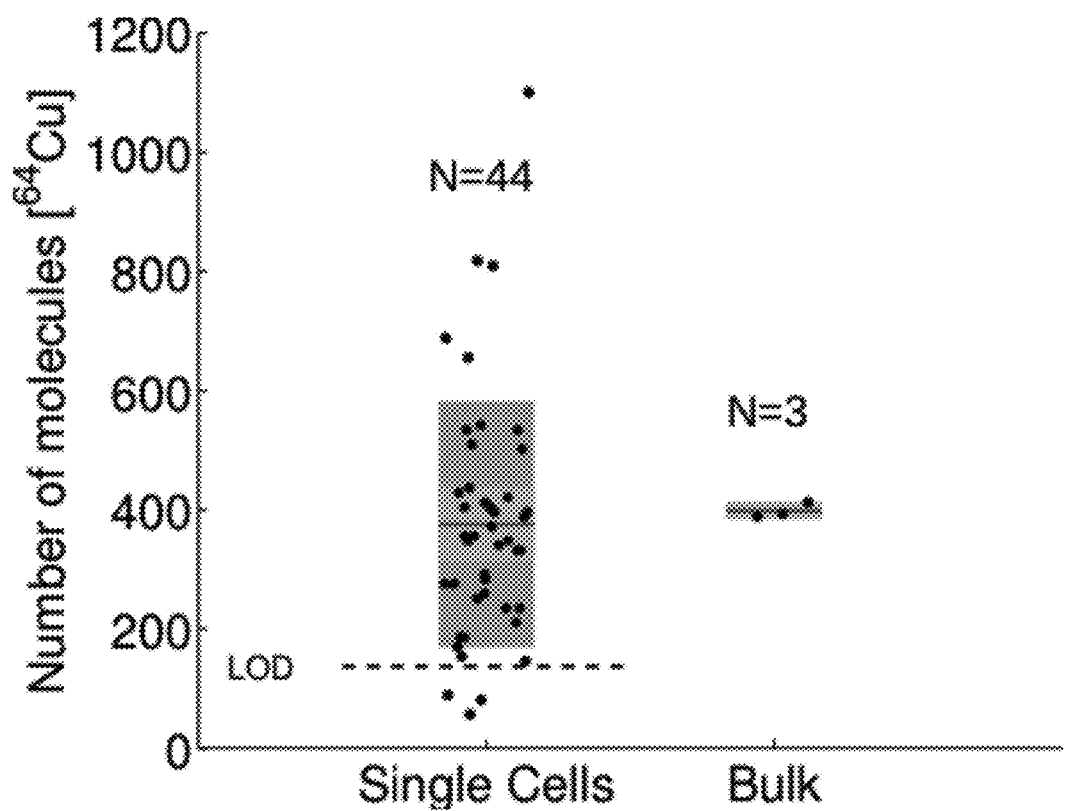
FIG. 1 shows (left) Uptake of 64Cu-labeled rituximab in single cells, measured by radioluminescence microscopy, compared to standard bulk gamma counting. (right) Radioluminescence micrograph, according to one embodiment of the invention.
Figure 2A:
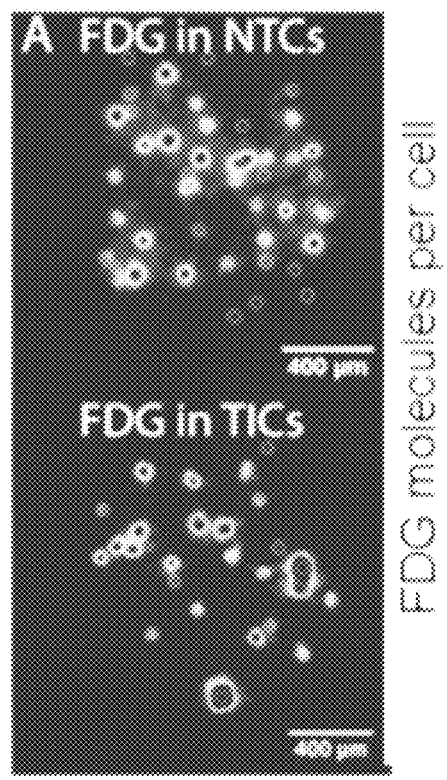
FIGS. 2A-2D show (FIG. 2A) Radioluminescence micrographs showing FDG uptake in non-tumorigenic cells (NTCs) and tumor-initiating cells (TICs)
Figure 2B:
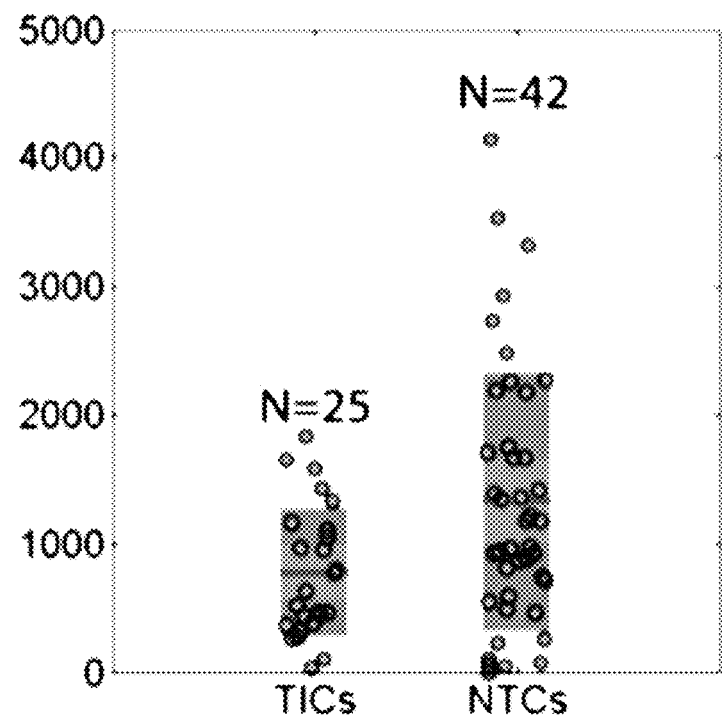
Figure 2C:
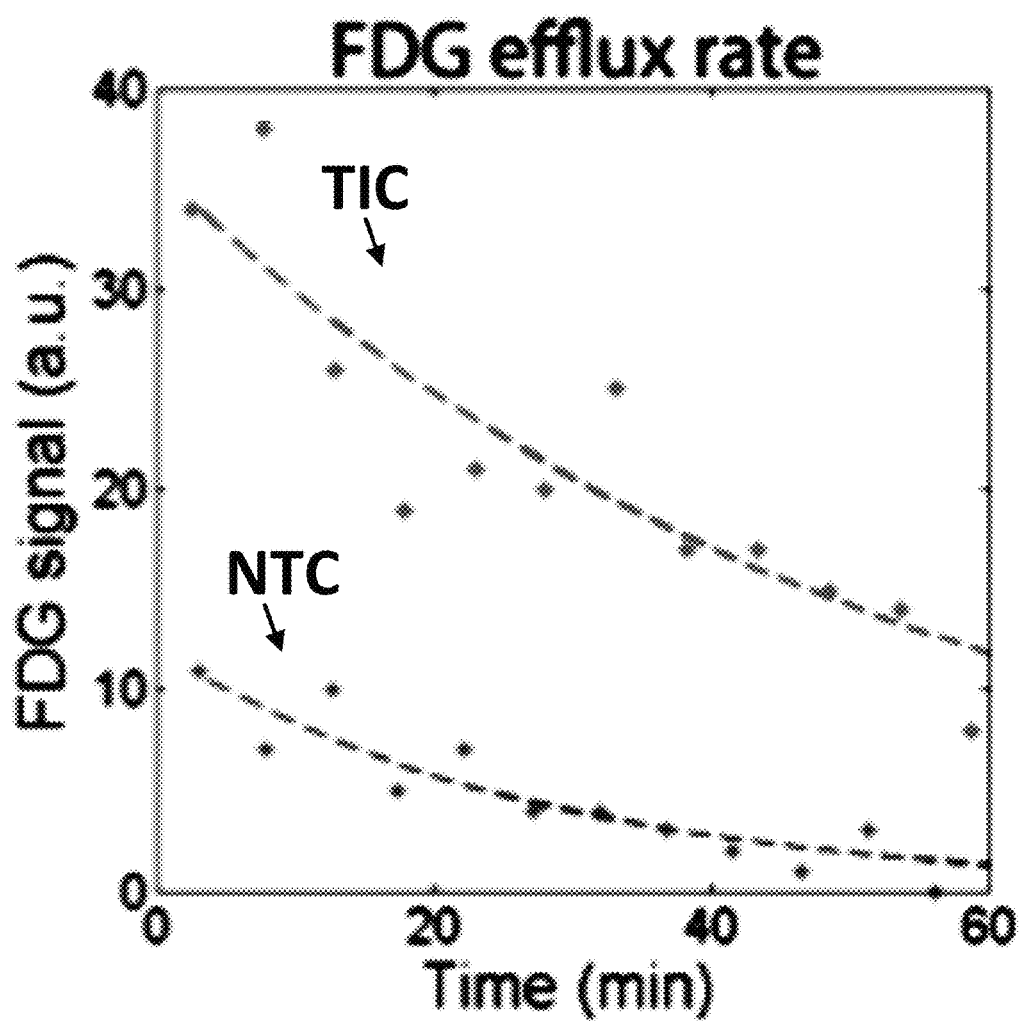
Figure 2D:
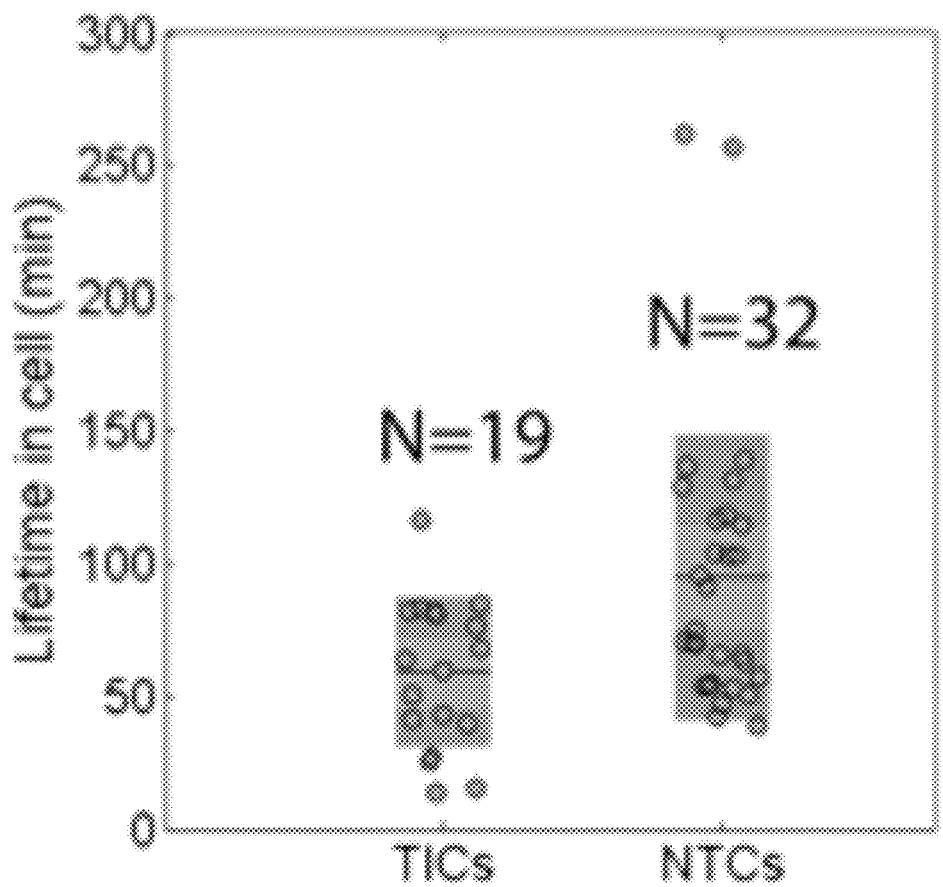

The current invention provides a high-throughput single-cell scintillation counting system that can sort cells on the basis of the uptake of a small radiolabeled molecule. Radiolabeled molecules are molecules in which one or more of the atoms are radioactive. Radionuclide detection methods (e.g., liquid scintillation counting, autoradiography) present the advantage that they can be used to detect a small molecule with high sensitivity, both in vitro and in vivo, without altering the biochemical activity of the labeled molecule, all of which make it the ideal approach for translational research. The inventors have recently shown that radionuclide detection can be extended to the single-cell level using a technique called radioluminescence microscopy. Single-cell measurements with this method provide information complementary to conventional bulk-scale assays. For instance, PET imaging of $^{64}$Cu-labeled rituximab (a monoclonal antibody used for non-Hodgkin lymphoma) provides in vivo pharmacokinetics at the tissue level, and radioluminescence microscopy of the same radiolabeled molecule measures the extent to which the binding of the drug varies from cell to cell (FIG. 1). These cellular variations cannot be assessed using conventional gamma counting of the bulk sample. Another application of this method was to assess uptake of 18F-fluorodeoxyglucose (FDG, a glucose analogue used clinically for oncologic imaging) in tumor-initiating cells (TICs) and non-tumorigenic cells (NTCs) (FIGS. 2A-2E). The cancer stem cell hypothesis postulates that a subpopulation of tumor cells (the TICs) possess self-renewing potential and can be partially identified by flow cytometry via cell surface markers. The inventors have shown that isolated TICs display FDG uptake distinct from NTCs due to a higher rate of FDG efflux, which is corroborated by the expression of drug-resistance-associated genes. This may have significant consequences for clinical decision-making given that FDG-PET is widely used for cancer diagnostics, staging and monitoring.

The contributions of this invention are significant because it will solve the two major shortcomings of radioluminescence microscopy. By switching from a "microscopy" to a "flow cytometry" paradigm, the current invention is capable of measuring up to one million cells in a single assay, as opposed to 100 cells currently, and to have the capability to sort and retrieve cells on the basis of their uptake of a radionuclide probe for subsequent molecular analysis. Together, these new capabilities have the potential to open new research avenues for interrogating normal and abnormal molecular processes in cancer and other diseases. For instance, it could help understand cellular differentiation in cancer by isolating sub-populations of cells that display unique metabolic signatures. It could also enable the mechanistic study of uptake and metabolism of drugs and other small molecules by single cells, revealing the entire histogram over many cells and not just bulk averages. Single-cell resolution is also critical for understanding tumor heterogeneity, especially considering that a tumor is made up of cells with many different phenotypes. Future studies using this invention may also help optimize the targeting of a specific phenotype within the tumor using a small-molecule therapeutic or imaging agent. Furthermore, pharmaceutical companies routinely use radiolabing to establish drug uptake at the tissue level, but they are not able to perform these studies at the single cell level. The invention solves this problem.

Methods that can analyze the heterogeneous states and phenotypes of single cells have been garnering increased research attention in recent years. Flow cytometry has long been used to interrogate cellular states by detecting fluorescence emissions from single cells, a process that however is not applicable to the many small-molecule compounds that are neither intrinsically fluorescent nor amenable to fluorescence labeling. The current invention relates to single cells interacting with virtually any small molecule. One embodiment of the invention utilizes the fact that many small molecules can be labeled with a beta-emitting radionuclide such as $^3$H, $^{11}$C, $^{14}$C, $^{18}$F, $^{32}$P, $^{33}$P, $^{68}$Ga, $^{89}$Zr, $^{64}$Cu, $^{131}$I or $^{35}$S. These radionuclides decay by emitting a charge particle, that is, an electron or a positron. In the past, measuring radionuclides within a flow cytometer posed a major challenge. Due to the high throughput required, each cell can only be measured for a few milliseconds, which is too short for a significant number of radioactive decays to occur. The current invention overcomes the deficiencies in the art by effectively converting and integrating ionizing radiation into an optical signal that can be readily measured within a standard flow cytometer.

The invention adds an extra dimension to flow cytometry by allowing the scientific instrument to probe not only conventional fluorescent probes but also one (and potentially more) radiolabeled probes. This is achieved by encapsulating cells with special materials that can store the energy emitted during radioactive decay and release it upon illumination with a suitable wavelength of light inside a standard flow cytometer.

Figure 3:
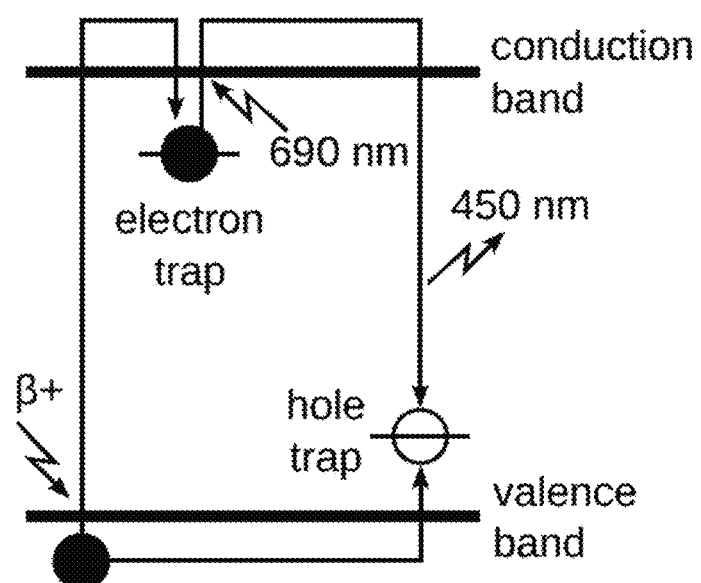
FIG. 3 shows optically stimulated luminescence, according to one embodiment of the invention.

The invention is a method by which radionuclide uptake can be measured in a conventional flow cytometer. According to one embodiment, photostimulable phosphors (PSP, a.k.a. storage phosphors) are used to record and store ionizing events emanating from single cells. PSP are semiconducting materials that exhibit high concentrations of trapping centers within their bandgap (FIG. 3). In this material, electrons excited by incident ionizing radiation can be captured by these trapping centers and may remain in that state for up to several weeks at room temperature. The information stored in the traps can be released by exposing crystal to a specific wavelength of light, upon which the trapped electrons recombine and luminesce.

Figure 4A:
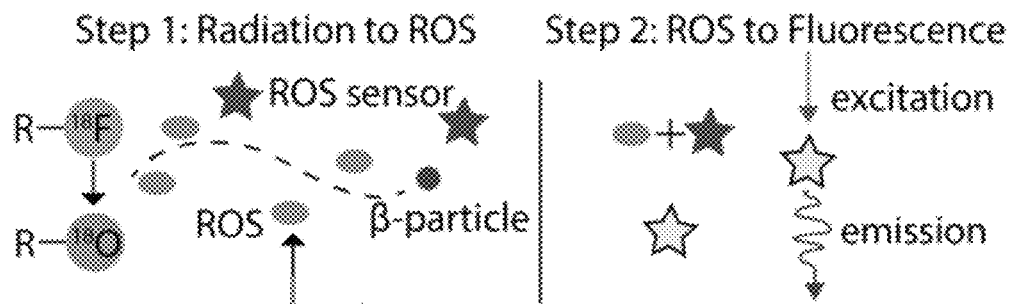
FIGS. 4A-4B show ionizing radiation converted to a fluorescent signal through a two-step process, where other products of radiolysis also include the .H radical and solvated electrons, according to the current invention.
Figure 4B:
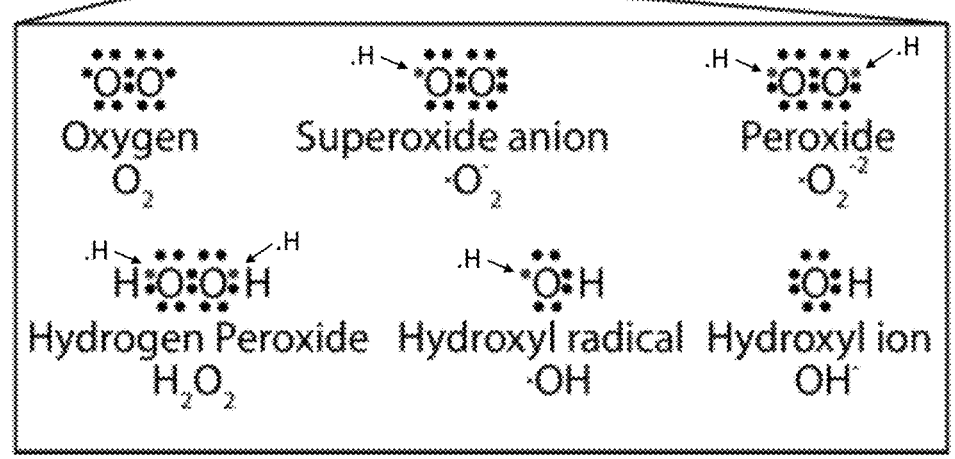

The current invention provides a robust method to measure the amount of beta-emitting radiolabeled molecule inside single cells using conventional flow cytometry technology. According to one embodiment, a system is provided that employs a chemical sensor of radiation, via reactive oxygen species (ROS sensor), to record and store ionizing events emanating from single cells in small droplets that contain one cell. Here, an ionizing particle creates reactive oxygen species as it travels through a solution (FIG. 4A, Step 1), which in turn will be captured by the ROS sensor (FIG. 4B, Step 2). This stored information can be read out at a later point in a fashion that is absolutely compatible with today's flow cytometry systems. These ROS sensors are encapsulated in droplets containing only either radiotracers (for validation purpose) or a single cell, which has previously taken up a radiolabeled molecule of interest (FIGS. 5A-5E). Adding a gelling agent will permanently bond the radiotracers together with the ROS sensor. According to one embodiment, the recorded ionizing radiation from the ROS sensors in each droplet can be read out using a commercial flow cytometry system. According to one aspect of the current invention, the molecules that are activated by the reactive oxygen species have molecules that include oxygen, superoxide anion, peroxide, hydrogen peroxide, or hydroxyl radical and hydroxyl ion.

In a further aspect of the invention, the chemical sensor has molecules that include a mixture of tertiary-butyl acrylate and maleimido-pyrene, a solution of Ferrous Benzoic acid Xylenol orange, a solution of ferrous sulfate, 2,7-Dichlorodihydrofluorescein (DCFH), 7-hydroxy-6-methoxy-coumarin (Scopoletin), 3.3. N-Acetyl-3,7-dihydroxyphenoxazine (Amplex Red), Homovanillic acid (4-hydroxy-3-methoxy-phenylacetic acid); Dihydrorhodamine 123 (DHR), 4-(9-Anthroyloxy)-2,2,6,6-tetramethyl-piperidine-1-oxyl, 1,3-Cyclohexanedione, Sodium terephthalate, Coumarin, coumarin-3-carboxylic acid, N-succinimidyl ester of coumarin-3-carboxylic acid, 2-[6-(4V-Hydroxy)phenoxy-3H-xanthen-3-on-9-yl]benzoic acid, 2-[6-(4V-amino)phenoxy-3H-xanthen-3-on-9-yl] benzoic acid, storage phosphors (e.g. $BaFBr:Eu^{2+}$ and $CsBr:Eu^{2+}$, silver halide particles, ratiometeric sensors, radiosensitive polymers, or cleavable FRET pair.

Figure 5A:
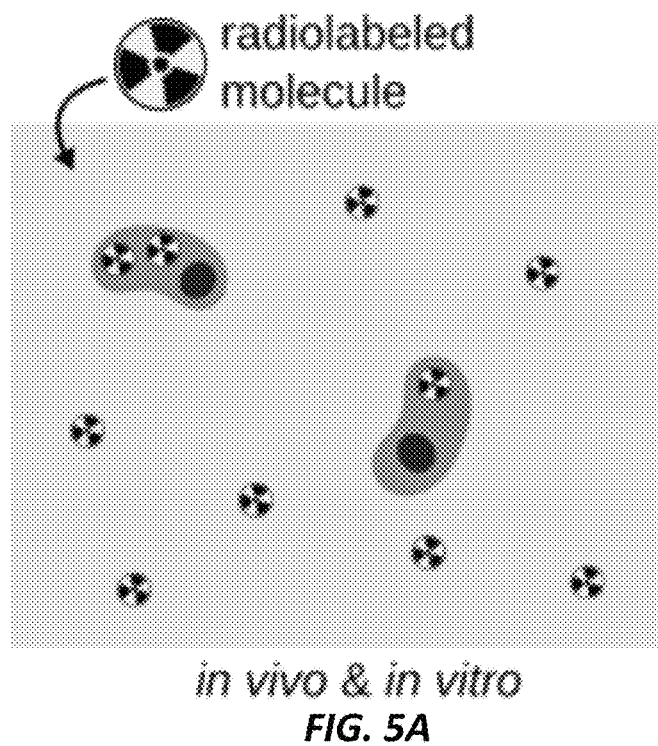
FIGS. 5A-5E show schematic drawings of the process according to one embodiment of current invention.
Figure 5B:
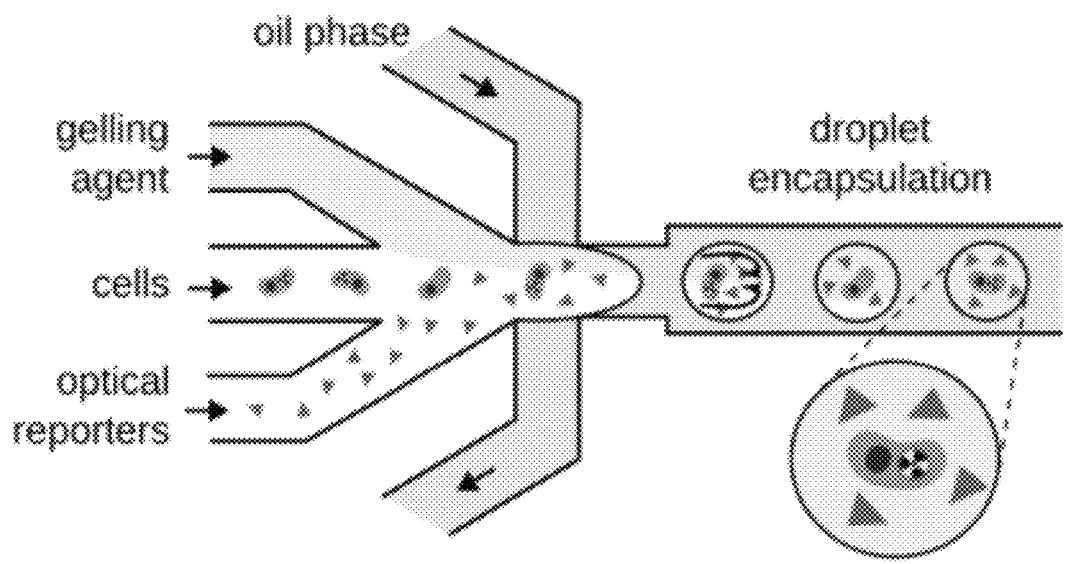
Figure 5C:
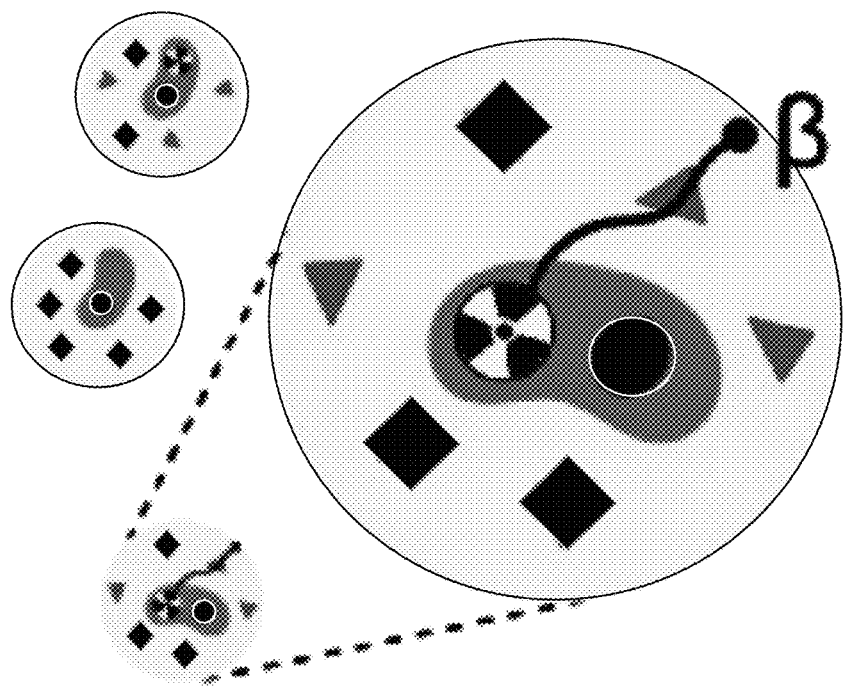
Figure 5D:
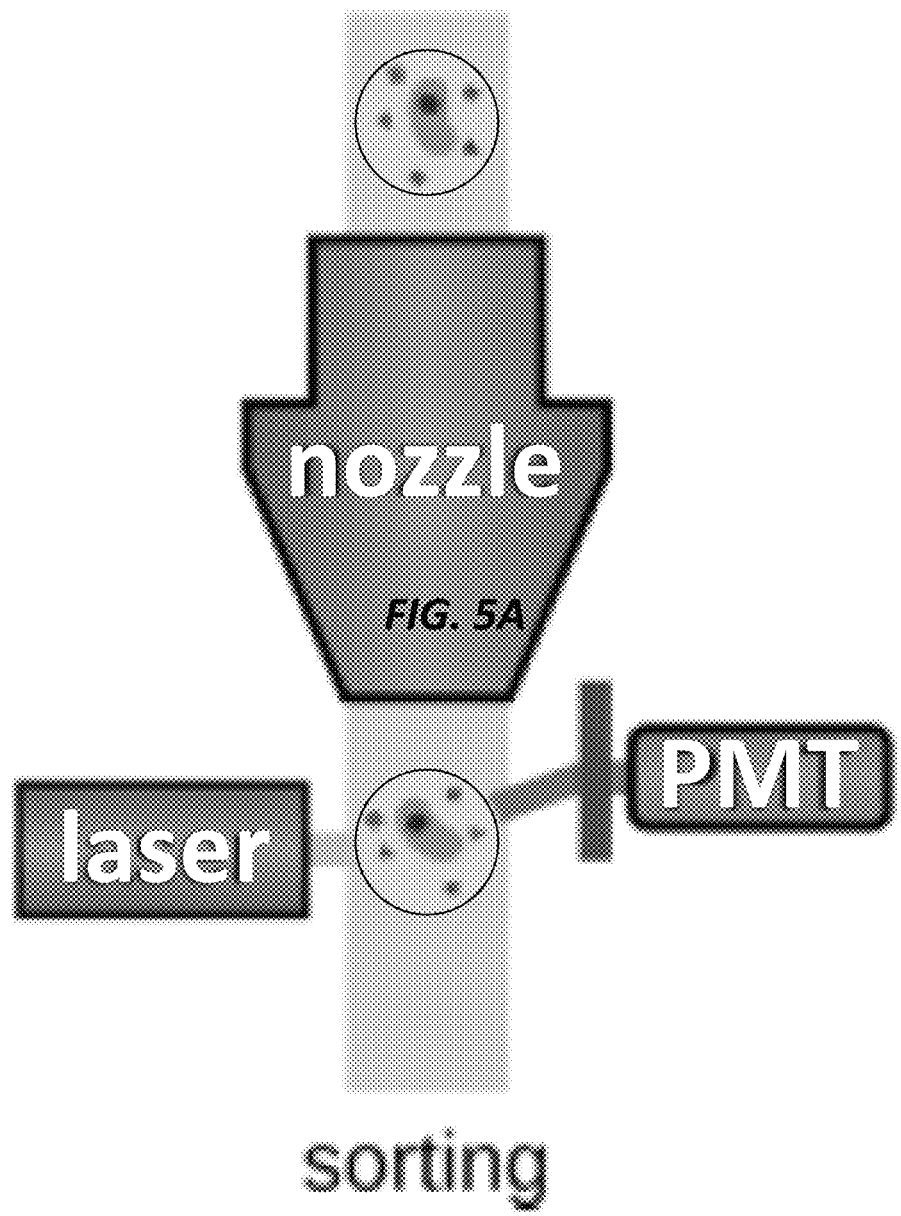
Figure 5E:
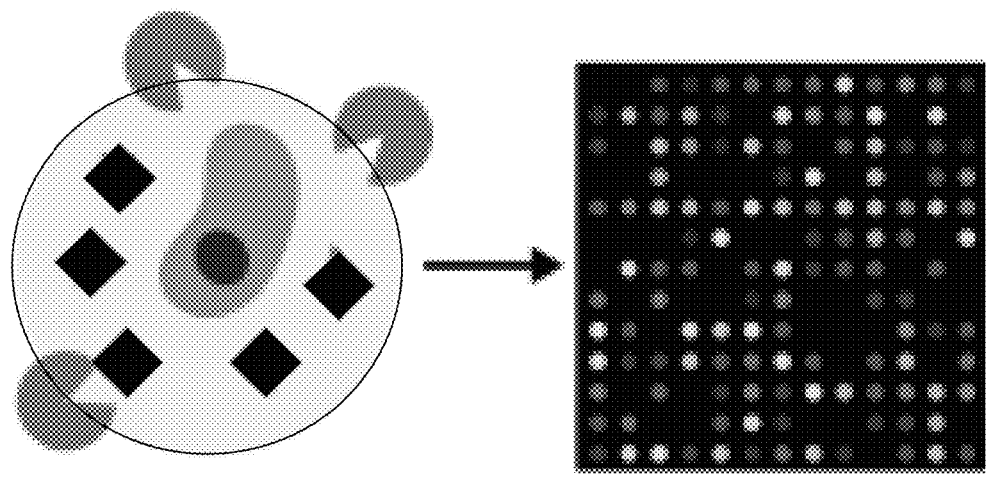

An exemplary embodiment of the current invention includes the steps shown in FIGS. 5A-5E. FIG. 5A shows the cells are incubated with a desired radiolabeled molecule. FIG. 5B shows the cells are suspended in alginate, matrigel, agarosede, gelatin, or any other gelling substance, then the PSP crystals are added, where these crystals can be nano-sized or micron-sized. Further shown is the formation of small droplets containing single-cells and a collection of PSP crystals, using any appropriate technology, including microfluidics. The droplets are then gelled, using appropriate methods such as temperature, pH change, or addition of calcium chloride, depending on the material. FIG. 5C shows the step of the radionuclide decaying in the encapsuant. The emitted beta particle ionizes the PSP crystals, resulting in electrons being trapped within the bandgap of the PSP. The droplets are then passed through a flow cytometer, as shown in FIG. 5D. The laser from the cytometer releases any trapped electrons, which recombine by emitting light in proportion to the dose (and therefore the amount of radionuclide) they have been exposed to. FIG. 5E show an optional aspect where, based on the signal measured, the droplets are sorted into various subgroups.

According to one aspect of the invention, the encapsulant can include a gelling agent in water, a gelling agent in oil, an oil droplet in water, and a water droplet in oil.

According to a further aspect of the invention, the chemical sensor is held in proximity to the cell by irreversibly being taken up by the cell rather than being encapsulated with the cell.

According to a further aspect of the invention, the chemical sensor is held in proximity to the cell by irreversibly binding it to the cell membrane rather than being encapsulated with the cell.

Variations of the invention include radiolabeling being done with 3H, 11C, 18F, 124I, 131I, 64Cu, 89Zr, 32P, 35S, 90Y, or any other beta-emitting radionuclide. Droplet formation can be done using various methods, the droplets can be made from a variety of materials, and PSP crystals can be made from a variety of materials.

According to one embodiment, the invention provides a method for counting beta-emitting a radiolabeled molecule inside single cells using conventional flow cytometry technology (or other suitable device), where the radionuclide uptake of up to one million cells can be individually counted. In another embodiment, the invention is capable of sorting and retrieving these cells on the basis of their uptake of a radionuclide molecule.

In another embodiment, silver halide crystals (e.g. silver bromide, chloride, iodide, or fluoride) are embedded with the cells in to the droplet to detect and record ionizing radiation within small droplets. These crystals are well known for their use in photographic or radiographic film. Upon exposure to a suitable developing agent, these crystals become darker and therefore the degree of darkening can be used to estimate the amount of radionuclide present in individual droplets. These silver halide crystals are used using a similar method as described previously, with the only difference that since they are not fluorescent, the information they contain is readout by measuring the absorption of the droplet. This can be done for example by measuring the forward and side scatter in a flow cytometer.

Another mechanism that can be used to measure radionuclide uptake in single cell-laden droplets involves special chemicals that are sensitive to radiation. One of these chemicals is ferrous sulfate (FeSO4), which is used clinically in radiation therapy in a technique called Fricke dosimetry. Upon exposure to ionizing radiation, $Fe^{2+}$ is oxidized to $Fe^{3+}$, which generates a blue color that can be detected optically. This colorimetric response has been shown to be linear with radiation dose. In one embodiment of this invention, $FeSO_4$ is embedded in the droplet together with cells and is used to measure the amount of radionuclide contained within the cells, by detecting a radiation-induced change in optical properties in individual droplets.

Another type of radiation-sensitive chemical are those that respond to ionizing radiation by polymerizing, thus resulting in a change in optical scatter. These materials are used clinically in radiation therapy in a technique called polymer gel dosimetry. Materials suitable for this technique include vinyl monomers such as N,N'-methylene-bis-acrylamide, acrylamide, Acrylic acid, Methacrylic acid, N-Vinylpirolidone, Hydroxyethylacrylate, and Poly(ethyl glycol) diacrylate. The unirradiated monomers are transparent, but increasing levels of radiation lead to polymerization of the monomer and increase of its optical absorption and scatter. These two optical properties can be measured using conventional flow cytometry or other suitable device. Thus, in one embodiment, the radiation sensitive monomers are embedded in the droplet together with cells and are used to measure the amount of radionuclide contained within the cells, by detecting a radiation-induced change in optical properties in individual droplets.

Other embodiments of the invention can also be implemented by using a device other than a flow cytometer. Several devices have been developed to optically analyze and sort droplets. Some devices utilize microfluidics technology to precisely manipulate droplets, using mechanical valves or dielectrophoresis to separate droplets. These microfluidics devices can be used in conjunction with lasers and optical detectors to manipulate and sort droplets based on their optical properties. Therefore, in one embodiment of the invention, a microfluidic device is used to analyze and sort droplets according to changes in optical properties that stem from ionizing radiation.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of sensing a radiolabeled molecule in cells, comprising:
   a) incubating an in vitro cell of interest to label said in vitro cell of interest with a radiolabeled molecule;
   b) encapsulating, in an encapsulant, said labeled in vitro cell of interest with a reactive oxygen species sensor (ROS sensor) to hold said labeled in vitro cell of interest in proximity to said ROS sensor within said encapsulant, wherein said ROS sensor is a non-fluorescent molecule, wherein said radiolabeled molecule decays while in said encapsulant to emit an energetic particle comprising an alpha particle or a beta particle wherein said energetic particle generates a reactive oxygen species (ROS) within said encapsulant that chemically reacts with said ROS sensor to yield a fluorescent molecule; and
   c) exposing, inside a droplet sorter or an optical analyzer, said fluorescent molecule to a suitable wavelength of light from a light source that is external to said encapsulant containing said fluorescent molecule, wherein said fluorescent molecule emits a different wavelength of light for detection, wherein said detected light is according to an amount of radionuclide uptake from said labeled in vitro cell of interest.

2. The method according to claim 1, wherein said ROS sensor includes molecules that are activated by said ROS comprising molecules selected from the group consisting of oxygen, superoxide anion, peroxide, hydrogen peroxide, hydroxyl radical, and hydroxyl ion.

3. The method according to claim 1, wherein said ROS sensor includes molecules selected from the group consisting of a mixture of tertiary-butyl acrylate and maleimidopyrene, a solution of Ferrous Benzoic acid and Xylenol (orange), a solution of ferrous sulfate, 2,7-Dichlorodihydrofluorescein (DCFH), 7-hydroxy-6-methoxy-coumarin (Scopoletin), 3.3. N-Acetyl-3,7-dihydroxyphenoxazine (Amplex Red), Homovanillic acid (4-hydroxy-3-methoxy-phenylacetic acid); Dihydrorhodamine 123 (DHR), 4-(9-Anthroyloxy)-2,2,6,6-tetramethylpiperidine-1-oxyl, 1,3-Cyclohexanedione, Sodium terephthalate, Coumarin, coumarin-3-carboxylic acid, N-succinimidyl ester of coumarin-3-carboxylic acid, 2-[6-(4V-Hydroxy)phenoxy-3H-xanthen-3-on-9-yl]benzoic acid, 2-[6-(4V-amino)phenoxy-3H-xanthen-3-on-9-yl] benzoic acid, storage phosphors (e.g. BaFBr:Eu2+ and CsBr:Eu2+), silver halide particles, ratiometric sensors, radiosensitive polymer, and cleavable FRET pair.

4. The method according to claim 1, wherein said radiolabeled molecules comprise molecules labeled with alpha or beta-emitting nuclides.

5. The method according to claim 4, wherein said beta-emitting nuclides are selected from the group consisting of $^{3}H$, $^{11}C$, $^{14}C$, $^{18}F$, $^{32}P$, $^{33}P$, $^{68}Ga$, $^{89}Zr$, $^{64}Cu$, $^{131}I$ and $^{35}S$.

6. The method according to claim 1, wherein said encapsulant is selected from the group consisting of a gelling agent in water, a gelling agent in oil, and a water droplet in oil.

7. The method according to claim 1, wherein said droplet sorter or optical analyzer is a device selected from the group consisting of a flow cytometer, a microfluidic device, a plate reader, and a microscope.

8. The method according to claim 1, wherein said ROS sensor is held in proximity to said in vitro cell by irreversibly being taken up by said in vitro cell or fixed to a cell membrane rather than being encapsulated with said in vitro cell.

9. The method according to claim 1 further comprises detecting an optical absorption signal in said ROS sensor induced by said radio molecule decay.

* * * * *